United States Patent
Burckhardt et al.

(10) Patent No.: US 9,593,196 B2
(45) Date of Patent: *Mar. 14, 2017

(54) ZINC(II) COMPLEX COMPOUNDS AS CATALYSTS FOR POLYURETHANE COMPOSITIONS

(71) Applicant: SIKA TECHNOLOGY AG, Baar (CH)

(72) Inventors: Urs Burckhardt, Zurich (CH); Rita Cannas, Dubendorf (CH)

(73) Assignee: SIKA TECHNOLOGY AG, Baar (CH)

( * ) Notice: Subject to any disclaimer, the term of this patent is extended or adjusted under 35 U.S.C. 154(b) by 196 days.

This patent is subject to a terminal disclaimer.

(21) Appl. No.: 14/358,846

(22) PCT Filed: Dec. 12, 2012

(86) PCT No.: PCT/EP2012/075203
§ 371 (c)(1),
(2) Date: May 16, 2014

(87) PCT Pub. No.: WO2013/087680
PCT Pub. Date: Jun. 20, 2013

(65) Prior Publication Data
US 2014/0296427 A1    Oct. 2, 2014

(30) Foreign Application Priority Data

Dec. 12, 2011  (EP) ................................ 11193061

(51) Int. Cl.
C07F 3/06   (2006.01)
C08G 18/22  (2006.01)
C08G 18/48  (2006.01)

(52) U.S. Cl.
CPC .............. C08G 18/222 (2013.01); C07F 3/06 (2013.01); C08G 18/4812 (2013.01)

(58) Field of Classification Search
CPC ...... C07F 3/06; C08G 18/222; C08G 18/4812
See application file for complete search history.

(56) References Cited

U.S. PATENT DOCUMENTS

| | | | |
|---|---|---|---|
| 4,231,921 A | | 11/1980 | Moser |
| 4,256,627 A | * | 3/1981 | Moser ............... C08L 101/00 524/100 |
| 4,377,690 A | | 3/1983 | Moser |
| 5,733,945 A | * | 3/1998 | Simpson ............ B01J 31/2234 521/124 |
| 2007/0249862 A1 | * | 10/2007 | Nagy ............... C08G 18/16 562/590 |
| 2011/0257286 A1 | * | 10/2011 | Maliverney ........ B01J 31/1805 521/170 |
| 2014/0303321 A1 | * | 10/2014 | Burckhardt ............. C07F 3/06 524/871 |

FOREIGN PATENT DOCUMENTS

| | | |
|---|---|---|
| CN | 101035825 A | 9/2007 |
| CN | 102223953 A | 10/2011 |
| EP | 0 000 487 A1 | 2/1979 |
| JP | H03-128930 A | 5/1991 |
| JP | H09-031151 A | 1/1997 |
| JP | A-9-208547 | 8/1997 |
| JP | A-9-220853 | 8/1997 |
| JP | 2003-292928 A | 10/2003 |
| JP | 2004269764 A | 9/2004 |
| JP | 2008-545058 A | 12/2008 |
| WO | 2006/018667 A1 | 2/2006 |
| WO | 2006/022899 A2 | 3/2006 |
| WO | 2007003966 A1 | 1/2007 |
| WO | 2010/043354 A1 | 4/2010 |

OTHER PUBLICATIONS

Dec. 1, 2015 Search Report issued in European Patent Application No. 12 801 553.4.
International Search Report issued in International Patent Application No. PCT/EP2012/075203 dated May 8, 2013.
International Preliminary Report on Patentability issued in International Patent Application No. PCT/EP2012/075203 dated Jun. 17, 2014.
Jul. 22, 2015 Office Action issued in Chinese Patent Application No. 201280060952.1.
Apr. 19, 2016 Chinese Office Action issued in Chinese Patent Application No. 201280060952.1.
Aug. 30, 2016 Office Action issued in Japanaese Patent Application No. 2014-546474.
Nov. 9, 2016 Office Action issued in Chinese Application No. 201280060952.1.

* cited by examiner

Primary Examiner — Patrick Niland
(74) Attorney, Agent, or Firm — Oliff PLC

(57) ABSTRACT

The present invention relates to zinc(II) complex compounds of the formula $Zn(L)_x(Y)_{2-x}$, wherein the ligand L has the formula (I). Such complex compounds are particularly suitable as catalysts for two-component polyurethane compositions. The invention also relates to two-component polyurethane compositions including at least one polyisocyanate as a first component, at least one polyol as a second component and at least one such zinc(II) complex compound as a catalyst. In addition, the invention relates to various uses of these two-component polyurethane compositions.

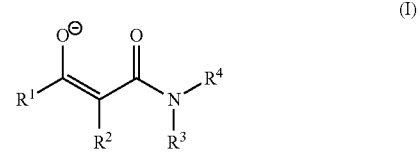

(I)

19 Claims, No Drawings

ZINC(II) COMPLEX COMPOUNDS AS CATALYSTS FOR POLYURETHANE COMPOSITIONS

TECHNICAL FIELD

The present invention relates to the field of polyurethane compositions and of catalysts for polyurethane compositions.

PRIOR ART

Polyurethane compositions have been known for a long time and are used in numerous fields. Conventionally, a distinction is made in professional circles between single-component and two-component polyurethane compositions. Single-component polyurethane compositions cure under the influence of atmospheric moisture. Two-component polyurethane compositions contain a curing agent component as second component which contains substantially polyamines and/or polyols. In both cases, isocyanate group-containing compounds or prepolymers are used.

To accelerate the curing, catalysts are added. Although numerous polyurethane catalysts are known, most, however, are not particularly selective with regard to the urethanization reaction, i.e., the reaction of alcohol OH groups with isocyanate groups; instead they also catalyze to varying degrees other reactions of the isocyanate group, such as allophanate and biuret formation or cyclotrimerization. In particular, the urethanization reaction is usually in competition with the reaction of the isocyanate groups with water, which leads to urea groups with release of gaseous carbon dioxide. In the case of numerous polyurethane compositions, particularly if they are used as an adhesive or a sealant, as a coating or a casting resin, this side reaction has a disruptive effect, since, during the curing, it leads to bubble formation and thus to inferior dimensional stability, lower adhesive strength, lower mechanical strength, an unsatisfactory appearance and to poorly reproducible results. The water responsible for bubble formation originates either from the residual water content of the components of the composition, in particular of the polyols and of the fillers, which, even after drying processes, remain moist to varying degrees and have a typical residual water content of 0.01 to 0.5 wt %, or, from the ambient moisture which penetrates into the composition by diffusion from the air or from the substrates, which occurs particularly at high atmospheric humidity, in the case of porous substrates and/or hydrophilic polyols such as the polyether polyols frequently used in practice. The amine catalysts that are used in many cases in practice, for example, tertiary amines, and tin catalysts, for example, dialkyl tin carboxylates, are precisely the ones that frequently lead to pronounced bubble formation. The residual water content in the polyurethane composition moreover has the effect that hydrolysis sensitive catalysts, such as bismuth carboxylates, become deactivated, for example, if the composition is put aside for a longer duration before use (storage), which has a negative influence on the curing rate and on the mechanical properties. In the case of some known catalysts, for example, dialkyl tin carboxylates, the resistance of the cured composition is moreover insufficient under thermal stress, wherein the catalyst causes a lowering of the molecular weight, i.e., a depolymerization, with loss of mechanical strength. Furthermore, many of the known catalysts are solid at room temperature and sparsely soluble in the polyurethane starting materials or in plasticizers, so that, for their use in compositions that cure at room temperature, organic solvents have to be used. Finally, some of the known catalysts, particularly those based on heavy metal compounds, are toxicologically unsafe.

It is also known to use zinc compounds, in particular polyurethane compositions, as catalysts for curable compositions. Usually, zinc(II) carboxylates are used, in particular zinc(II) bis(2-ethylhexanoate) or zinc(II) bis(neodecanoate). Although such zinc compounds are in principle advantageous as catalysts, since, on the one hand, in contrast to compounds of transition metals, for example, vanadium, iron, manganese or cobalt, they are colorless or only slightly colored and they cause hardly any discoloration, and, on the other hand, in contrast to the compounds of the other $d^{10}$ transition metals, cadmium and mercury, as well as neighboring main group metals, such as tin, lead or antimony, they are largely toxicologically safe. However, the catalytic activity of zinc(II) carboxylates with regard to the urethanization reaction is comparatively low, so that, in practice, zinc(II) carboxylates can usually be used only as auxiliary catalysts, for example, in combination with bismuth(III) or zirconium (IV) carboxylates as a main catalyst.

REPRESENTATION OF THE INVENTION

The problem of the present invention is to eliminate the above-described disadvantages of the prior art. In particular, the problem of the present invention is to provide a catalyst which leads to an improvement of the following properties or to a balanced ratio.

The catalyst should be characterized by high catalytic activity and selectivity with regard to the urethanization reaction, i.e., the reaction of alcohol OH groups with isocyanate groups, and thus it should make possible a rapid construction—disturbed as little as possible by moisture—of a mechanically high-quality polyurethane polymer from polyfunctional alcohols (polyols) and polyisocyanates. In addition, the catalyst should have a sufficient hydrolysis resistance in order to be preserved under the usual storage conditions, i.e., at room temperature or at slightly increased temperatures, for several months in a residual water-containing polyol composition without strong loss of activity. Moreover, the catalyst should lower the thermal resistance of the cured polyurethane polymer as little as possible. In addition, the catalyst should be liquid at room temperature or at slightly increased temperatures or it should be readily soluble in the polyurethane starting materials or in plasticizers, so that it can be used simply in solvent-free systems that cure at room temperature. Finally, the catalyst should have the lowest possible toxicity.

Surprisingly, a novel zinc(II) complex compound according to claim 1 having the desired properties has now been discovered. The novel zinc(II) complex compound has formula $Zn(L)_x(Y)_{2-x}$, where x stands for 1 or 2, Y for a ligand with a single negative charge, and L for a ligand of formula (I),

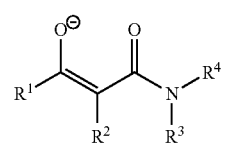

where $R^1$ and $R^2$, independently of one another, stand for a hydrogen residue, for a monovalent saturated or unsaturated hydrocarbon residue having 1 to 10 carbon atoms, or together stand for a bivalent alkylene residue having 3 to 6 carbon atoms, and $R^3$ and $R^4$, independently of one another, stand for a hydrogen residue, a monovalent saturated hydrocarbon residue, which optionally contains heteroatoms, having 1 to 12 carbon atoms, or together stand for a bivalent alkylene residue, which optionally contains heteroatoms, having 3 to 6 carbon atoms.

The ligand L of formula (I) formally has a single negative load delocalized over the 1,3-ketoamide structure. Therefore, it can be drawn in the form of different resonance structures, for example, in the form of the resonance structures represented below. All the possible resonance structures of the ligands L of formula (I) are considered to be equivalent in the context of the present invention.

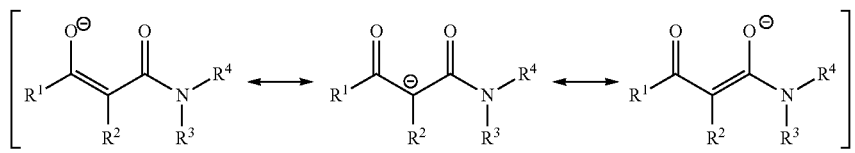

The ligand Y represents any ligand having a single negative charge, in particular a suitable organic anion, preferably a carbonylate, particularly preferably a 1,3-dicarbonylate, for example, acetylacetonate or 2,2,6,6-tetramethylheptane-3,5-dionate.

The zinc(II) complex compound of formula $Zn(L)_x(Y)_{2-x}$ according to the invention with zinc as a central atom and coordinatively bound ligands L and optionally Y is neutral and it contains one or two ligands L of formula (I).

In the zinc(II) complex compound of formula $Zn(L)_x(Y)_{2-x}$ according to the invention, x preferably stands for 2, since these complex compounds are particularly stable. The two ligands L of formula (I) can be identical or different. It is particularly preferable here to have two identical ligands L of formula (I).

In formula (I), $R^1$ and $R^2$ independently of one another stand for a hydrogen residue, for a monovalent saturated or unsaturated hydrocarbon residue having 1 to 10 carbon atoms, or together stand for a bivalent alkylene residue having 3 to 6 carbon atoms.

The monovalent saturated hydrocarbon residue having 1 to 10 carbon atoms is preferably an alkyl residue having 1 to 4 carbon atoms, in particular a methyl or a butyl residue. These have the advantage that the complex compound consequently tends to be liquid or readily soluble. The monovalent unsaturated hydrocarbon residue also preferably is an aryl residue, in particular a phenyl residue.

It is particularly preferable for $R^2$ to be a hydrogen residue, since the complex compound as a result tends to be particularly stable.

A bivalent alkylene residue having 3 to 6 carbon atoms is understood to be a residue of formula $—(CH_2)_n—$, where n stands for 3 to 6, preferably 3 to 4, and particularly preferably 3.

$R^1$ and $R^2$ together preferably form a bivalent alkylene residue having 3 to 4 carbon atoms, in particular 3 carbon atoms.

$R^3$ and $R^4$ independently of one another stand for a hydrogen residue, a monovalent saturated hydrocarbon residue, which optionally contains heteroatoms; having 1 to 12 carbon atoms, or together stand for a bivalent alkylene residue, which optionally contains heteroatoms, having 3 to 6 carbon atoms.

The monovalent saturated hydrocarbon residue having 1 to 12 carbon atoms is preferably an alkyl residue having 1 to 8 carbon atoms, particularly preferably a methyl, ethyl, propyl, isopropyl, butyl, isobutyl, hexyl, 2-methylpentyl, octyl- or 2-ethylhexyl residue. This has the advantage that the complex compound as a result tends to be liquid or readily soluble. The monovalent saturated hydrocarbon residue having 1 to 12 carbon atoms can preferably be a cycloalkyl residue having 5 to 6 carbon atoms, particularly preferably 6 carbon atoms. The monovalent saturated hydrocarbon residue with heteroatoms is preferably a hydroxyalkyl residue having 1 to 4 carbon atoms, particularly preferably a 2-hydroxyethyl or 2-hydroxypropyl residue. This has the advantage that the complex compound as a result tends to be liquid or readily soluble, and the ligand can be covalently integrated into the polymer during the curing. It is also preferable to use an alkyl ether residue having 1 to 4 carbon atoms, particularly preferably a 2-methoxyethyl or 2-(2-methoxy)ethoxyethyl residue, since the complex compound as a result tends to be liquid or readily soluble.

$R^3$ together with $R^4$ can also preferably form a bivalent alkylene residue of formula $—(CH_2)_n—X—(CH_2)_n—$ with X=O, NR, where R is a monovalent alkyl residue having 1 to 4 carbon atoms or S, and n=2 to 4. Particularly preferably n=2 and X=O or NR.

The selection of the preferred residue in the ligands L of formula (I) is based, for example, on the fact that the corresponding 1,3-ketoamides, which are used as starting substances for preparing the zinc(II) complex compounds of formula $Zn(L)_x(Y)_{2-x}$ according to the invention, are easy to prepare and/or commercially available and consequently inexpensive.

It is preferable to use zinc(II) complex compounds of formula $Zn(L)_2$ having two identical ligands L of formula (I), where $R^1$ to $R^4$ have the meanings indicated in the table.

| | $R^1$ | $R^2$ | $R^3$ | $R^4$ |
|---|---|---|---|---|
| (1) | Alkyl residue having 1-4 carbon atoms | Hydrogen residue | Alkyl residue having 1-8 carbon atoms | Alkyl residue having 1-8 carbon atoms |
| (2) | Phenyl residue | Hydrogen residue | Alkyl residue having 1-8 carbon atoms | Alkyl residue having 1-8 carbon atoms |
| (3) | Alkyl residue having 1-4 carbon atoms | Hydrogen residue | Alkyl ether residue having 1-4 carbon atoms | Alkyl ether residue having 1-4 carbon atoms |
| (4) | Alkylene residue having 3-6 carbon atoms | | Alkyl residue having 1-8 carbon atoms | |
| (5) | Alkyl residue having 1-4 carbon atoms | Hydrogen residue | Alkylene residue of formula $—(CH_2)_n—X—(CH_2)_n—$ with X = O or NR and n = 2 | |
| (6) | Alkyl residue having 1-4 carbon atoms, | Hydrogen residue | Cycloalkyl residue having 5-6 carbon atoms | Alkyl residue having 1-8 carbon atoms |

-continued

| R¹ | R² | R³ | R⁴ |
|---|---|---|---|
| (7) Alkyl residue having 1-4 carbon atoms | Hydrogen residue | Alkyl residue having 1-8 carbon atoms | Cycloalkyl residue having 5-6 carbon atoms |
| (8) Phenyl residue | Hydrogen residue | \multicolumn{2}{l}{Alkylene residue of formula (—CH$_2$)$_n$—X—(CH$_2$)$_n$— with X = O or NR and n = 2} | |

In a preferred embodiment, the zinc(II) complex compound of formula $Zn(L)_x(Y)_{2-x}$ according to the invention is not the Zn-II chelate of 2,2,6,6-tetramethyl-4-[N-n-butylamine-N(1',3'-dioxobutyl)] piperidine enolate.

The preparation of the zinc(II) complex compound of formula $Zn(L)_x(Y)_{2-x}$ according to the invention is carried out by reacting a 1,3-ketoamide of formula

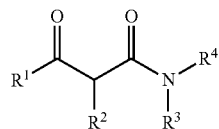

with $R^1$, $R^2$, $R^3$ and $R^4$, as defined above, with a zinc(II) salt or zinc(II) complex. It is preferable to use zinc chloride, zinc acetate and Zn(II) bis(acetylacetonate), particularly preferably zinc(II) bis(acetylacetonate).

The 1,3-ketoamide here can be used in stoichiometric or above stoichiometric quantities. In the case of an above stoichiometric use of the 1,3-ketoamide, the zinc(II) complex compound according to the invention tends to have an increased hydrolysis stability and a lower viscosity. It is preferable for the stoichiometric ratio between the zinc(II) salt or zinc(II) complex and 1,3-ketoamide to be in the range from 1:2 to 1:6.

The preferably dried zinc(II) salt or zinc(II) complex is mixed with the 1,3-ketoamide and the mixture is heated preferably under stirring for 1 to 24 hours, preferably for approximately 3 hours, at a temperature of 50 to 130° C., particularly at approximately 80° C. Subsequently, volatile components are removed from the reaction mixture, preferably in a vacuum.

The preferably dried zinc(II) salt or zinc(II) complex can also be reacted in a high boiling point organic solvent, in particular a tetraethylene glycol dimethyl ether (TEGDME), with 1,3-ketoamide and heated preferably under stirring for 1 to 24 hours, preferably for approximately 3 hours, at 50 to 130° C., preferably at approximately 80° C. The reaction mixture is then cooled preferably to room temperature.

The zinc(II) complex compounds according to the invention can be used as a catalyst for curable compositions, preferably for polyurethane compositions. The zinc(II) complex compound according to the invention accelerates the curing of curable compositions, which comprise reactive groups that are capable of undergoing crosslinking reactions. It is particularly preferable for the zinc(II) complex compound according to the invention to accelerate the curing of two-component polyurethane compositions, which crosslink with themselves and if applicable under the influence of a moisture via blocked and in particular free isocyanate groups. In the process, the urethanization reaction, i.e., the reaction of isocyanate groups with alcohol OH groups, is accelerated above all. The compositions to be crosslinked can also contain additional reactive groups that are capable of undergoing crosslinking reactions, such as alkoxysilane groups, in particular. Said groups are preferably trialkoxysilane groups as contained in silane adhesives, for example.

The zinc(II) complex compounds according to the invention can be used advantageously as a catalyst in a two-component polyurethane composition. The latter comprises, in addition to the zinc(II) complex compound according to the invention, a polyol as first component as well as a polyisocyanate as second component.

The term "two-component" denotes a composition in which the constituents thereof are in the form of two different components, which are stored in containers that are separate from one another and that are each individually storage-stable. It is only shortly before or during the application of the composition that the two components are mixed with one another, after which the mixed composition is cured, wherein the curing under some circumstances occurs or is completed only due to the influence of moisture and/or increased temperature.

Substance names, such as polyol or polyisocyanate, that start with "poly" denote substances that formally contain two or more of the functional groups that occur in their name per molecule.

The term "polyisocyanate" comprises compounds with two or more isocyanate groups, independently of whether they are polymers that comprise monomeric diisocyanates, oligomeric polyisocyanates or isocyanate groups.

A suitable polyisocyanate is, for example, a polyisocyanate in the form of a monomeric diisocyanate or triisocyanate or of an oligomer of a monomeric diisocyanate or of a derivative of a monomeric diisocyanate.

Suitable monomeric diisocyanates or triisocyanates are, for example, 1,4-tetramethylene diisocyanate, 2-methylpentamethylene-1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane-1,3- and -1,4-diisocyanate, 1-methyl-2,4- and -2,6-diisocyanatocyclohexane and any desired mixtures of these isomers, 1-isocyanato-3,3,5-trimethyl-5-isocyanatomethyl-cyclohexane (=isophorone diisocyanate or IPDI), perhydro-2,4'- and -4,4'-diphenylmethane diisocyanate (HMDI), 1,4-diisocyanato-2,2,6-trimethylcyclohexane (TMCDI), 1,3- and 1,4-bis-(isocyanatomethyl) cyclohexane, m- and p-xylylene diisocyanate (m- and p-XDI), m- and p-tetramethyl-1,3- and -1,4-xylylene diisocyanate (m- and p-TMXDI), bis-(1-isocyanato-1-methylethyl)naphthalene, dimer and trimer fatty acid isocyanates, such as 3,6-bis-(9-isocyanatononyl)-4,5-di-(1-heptenyl)cyclohexene (dimeryl diisocyanate), α,α,α',α',α'',α''-hexamethyl-1,3,5-mesitylene triisocyanate, 2,4- and 2,6-toluoylene diisocyanate and any mixtures of these isomers (TDI), 4,4'-, 2,4'- and 2,2'-diphenylmethane diisocyanate and any mixtures of these isomers (MDI), mixtures of MDI and MDI homologs (polymer MDI or PMDI), 1,3- and 1,4-phenylene diisocyanate, 2,3,5,6-tetramethyl-1,4-diisocyanatobenzene, 1,5-naphthalene diisocyanate (NDI), 3,3'-dimethyl-4,4'-diisocyanatodiphenyl (TODI), dianisidine diisocyanate (DADI), 1,3,5-tris-(isocyanatomethyl)benzene, tris-(4-isocyanatophenyl)methane, and tris-(4-isocyanatophenyl)thiophosphate.

Preferred polyisocyanates are commercial diisocyanates. It is particularly preferable to use HDI, IPDI, TDI and MDI as well as oligomers of polyurethane polymers that contain diisocyanates and isocyanate, (NCO prepolymers).

As polyols one can use, for example, the following commercial polyols or mixtures thereof:

Polyoxyalkylene polyols, also referred to as polyether polyols or oligoetherols, which are polymerization products of ethylene oxide, 1,2-propylene oxide, 1,2- or 2,3-butylene oxide, oxetane, tetrahydrofuran or mixtures thereof, optionally polymerized using a starter molecule with two or more active hydrogen atoms, such as, for example, water, ammonia or compounds with several OH or NH groups, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexane dimethanol, bisphenol A, hydrogenated bisphenol A, 1,1,1-trimethylolethane, 1,1,1-trimethylolpropane, glycerol, aniline as well as mixtures of the above-mentioned compounds. It is also possible to use both polyoxyalkylene polyols having a low degree of unsaturation (measured according to ASTM D-2849-69 and indicated in milliequivalent unsaturation per gram polyol (mEq/g)), prepared, for example, using the so-called Double Metal Cyanide Complex catalysts (DMC catalysts) and also polyoxyalkylene polyols having a higher degree of unsaturation, produced, for example, using anionic catalysts, such as, NaOH, KOH, CsOH or alkali alcoholates.

Particularly suitable are polyoxyalkylenediols or polyoxyalkylenetriols, in particular polyoxyethylene- and polyoxypropylenediols and -triols. Especially suitable are polyoxyalkylenediols and -triols having a degree of unsaturation of less than 0.02 mEq/g and a molecular weight in the range of 1000-30,000 g/mol, as well as polyoxypropylenediols and -triols having a molecular weight of 400-8000 g/mol.

Also particularly suitable are so-called ethylene oxide-terminated ("EO-endcapped," ethylene oxide-endcapped) polyoxypropylene polyols. The latter are special polyoxypropylene polyoxyethylene polyols prepared, for example, by further alkoxylating pure polyoxypropylene polyols, in particular polyoxypropylenediols and -triols, with ethylene oxide after the completion of the polypropoxylation reaction, which as a result have primary hydroxyl groups.

Styrene acrylonitrile or acrylonitrile methyl methacrylate-grafted polyether polyols.

Polyester polyols, also referred to as oligoesterols, prepared by known methods, in particular by the polycondensation of hydroxycarboxylic acids or the polycondensation of aliphatic and/or aromatic polycarboxylic acids with bivalent or polyvalent alcohols.

Particularly suitable polyester polyols are those that are prepared from bivalent to trivalent alcohols, in particular bivalent alcohols, such as, for example, ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexanedimethanol, dimer fatty acid dial (dimerdiol), hydroxypivalic acid neopentyl glycol ester, glycerol, 1,1,1-trimethylolpropane or mixtures of the above-mentioned alcohols, with organic dicarboxylic or tricarboxylic acids, in particular dicarboxylic acids, or their anhydrides or esters, such as, for example, succinic acid, glutaric acid, adipic acid, trimethyl adipic acid, suberic acid, azelaic acid, sebacic acid, dodecanedicarboxylic acid, maleic acid, fumaric acid, dimer fatty acid, phthalic acid, phthalic acid anhydride, isophthalic acid, terephthalic acid, dimethyl terephthalate, hexahydrophthalic acid, trimellitic acid and trimellitic acid anhydride, or mixtures of the above-mentioned acids, as well as polyester polyols from lactones, such as, for example, from ε-caprolactone, and starters such as the above-mentioned bivalent or trivalent alcohols.

Polycarbonate polyols, as from reacting, for example, the above-mentioned alcohols—used for the construction of the polyester polyols—with dialkyl carbonates, diary carbonates or phosgene.

Block copolymers bearing at least two hydroxyl groups, which have at least two different blocks with polyether, polyester and/or polycarbonate structure of the above-described type, in particular polyether polyester polyols.

Polyacrylate and polymethacrylate polyols.

Polyhydroxy-functional fats and oils, for example, natural fats and oils, particularly castor oil; or so-called oleochemical polyols—prepared by chemical modification of natural fats and oils —, for example, the epoxy polyesters or epoxy polyethers obtained by epoxidation of unsaturated oils followed by ring opening with carboxylic acids or alcohols, or the polyols obtained by hydroformylation and hydrogenation of unsaturated oils; or polyols obtained from natural fats and oils by degradation processes, such as alcoholysis or ozonolysis and subsequent chemical linking, for example, by transesterification or dimerization, of the resulting degradation products or derivatives thereof. Suitable degradation products of natural fats and oils are, in particular, fatty acids and fatty alcohols as well as fatty acid esters, in particular methyl esters (FAME), which can be derivatized, for example, by hydroformylation and hydrogenation to form hydroxy fatty acid esters.

Polyhydrocarbon polyols, also referred to as oligo hydrocarbonols, such as, for example, polyhydroxy functional polyolefins, polyisobutylenes, polyisoprenes; polyhydroxy functional ethylene-propylene, ethylene-butylene or ethylene-propylene-diene copolymers; polyhydroxy functional polymers of dienes, in particular of 1,3-butadiene, which can in particular also be produced by anionic polymerization; polyhydroxy functional copolymers of dienes, such as 1,3-butadiene or diene mixtures, and vinyl monomers, such as styrene, acrylonitrile, vinyl chloride, vinyl acetate, vinyl alcohol, isobutylene and isoprene, for example, polyhydroxy functional acrylonitrile/butadiene copolymers, as can be produced, for example, from epoxides or amino alcohols and carboxyl-terminated acrylonitrile/butadiene copolymers; as well as hydrogenated polyhydroxy functional polymers or copolymers of dienes.

The mentioned polyols preferably have an average molecular weight of 250-30,000 g/mol, in particular of 400-20,000 g/mol, and furthermore they preferably have an average OH functionality in the range from 1.6 to 3.

The term "molecular weight" in the case of oligomers or polymers always refers to the average molecular weight $M_n$.

It is particularly preferable to use polyether polyols, preferably polypropylene polyols and polyethylene-polypropylene mixed polyols, as well as polyester polyols and polycarbonate polyols.

The zinc(II) complex compound according to the invention is preferably located in the first component, which has the advantage that the storage stability (shelf life) of the polyisocyanate, which is sensitive to catalytically acting compounds, is not affected in the second component.

The zinc(II) complex compound according to the invention can be used as the sole catalyst, or also together with other catalysts, such as, for example, bismuth, tin or zirconium compounds, or tertiary amines.

The two-component polyurethane composition according to the invention can optionally contain additional typically used auxiliary substances and additives, for example, pigments, plasticizers or diluents, curing agents, crosslinking agents, chain elongation agents, additional catalysts, adhesive promoters, stabilizers, rheological aids and desiccants, etc.

The zinc(II) complex compound according to the invention, in terms of quantity of elemental zinc, is preferably present in the two-component polyurethane composition according to the invention in a quantity of 0.001 to 1 wt %, particularly preferably in a quantity of 0.005 to 0.5 wt %, and quite particularly preferably in a quantity of 0.01 to 0.2 wt %, relative to the weight of the composition. Excessively large quantities lead to too short an open time or processing time of the composition, whereas the use of smaller quantities has the disadvantage that the composition is catalyzed too weakly and it thus cures too slowly, incompletely and/or defectively. In the two-component polyurethane composition according to the invention, the zinc(II) complex compound according to the invention represents 0.015 to 15, preferably 0.075 to 7.5, and particularly preferably 0.15 to 3 mmol equivalents of zinc atoms per 100 g of the composition.

As already mentioned above, with regard to the urethanization reaction, the zinc(II) complex compound according to the invention is relatively active and also relatively selective. In comparison to zinc(II) carboxylates, the zinc(II) complex compound according to the invention is characterized by a clearly higher catalytic activity. In general, the curing of the two-component polyurethane composition according to the invention occurs rapidly, in particular with clearly shorter curing times than when Zn(II) carboxylates are used. However, the selectivity of the zinc(II) complex compound according to the invention does not suffer due to the increased activity; the curing occurs without formation of bubbles, even under disadvantageous conditions, such as high temperature, high ambient moisture and a high residual water content of the compound as well as in the case of the use of polyols with secondary OH groups or hydrophilic polyols. The zinc(II) complex compound according to the invention is relatively stable thermally and hydrolytically and even in a polyol containing residual water it decomposes only slowly and thus keeps its catalytic activity even in the case of a longer storage time. The use of the zinc(II) complex compound according to the invention still leads to a satisfactory stability of the cured polyurethane composition even under thermal exposure. Furthermore, the zinc(II) complex compound according to the invention is liquid at room temperature and/or readily soluble in plasticizers or polyols, and thus it can be used simply in systems that cure at room temperature, and in particular without the use of volatile organic solvents (VOC). Finally, the zinc(II) complex compound according to the invention is only slightly colored and it leads to hardly any discoloration of the cured polyurethane composition; it also has a relatively low toxicity.

The two-component polyurethane composition according to the invention can be used in numerous fields, for example, as a casting composition, sealant, adhesive; covering, coating, paint, primer, hard foam, soft foam, molded part, elastomer, fiber, film or membrane for applications in construction and industry, for example, as an electro casting composition, spackling compound, seam sealant, cavity sealant, joint sealant, assembly adhesive, car body adhesive, plate adhesive, sandwich element adhesive, laminating adhesive, laminate adhesive, packaging adhesive, wood adhesive, parquet adhesive, anchoring adhesive, bottom covering and coating, balcony and roof coating, concrete protection coating, parking garage coating, pipe coating, corrosion protection coating, textile coating, wood paint, decoration paint, primer, furniture foam, padding foam, filter foam, insulation foam, sound insulation foam, sealing foam, packaging foam, car body foam, model building plate, damping element, sealing element, tires, rolls, bearings, rollers, conveyor belt, elastic threads, shoe soles, casings, window profile section, implant, foam rubber, etc.

Preferred application fields are casting compositions, sealants, adhesives, coverings, coatings, paints, primers, molded parts and elastomers for applications in construction and industry.

In addition to its use in two-component polyurethane compositions, the zinc(II) complex compound according to the invention can also be used as a catalyst or cocatalyst in other curable compositions, for example, in single-component polyurethane compositions, in epoxy resins, acrylates and silicones.

In addition to the use as a catalyst, other applications in which zinc compounds are used are in principle also conceivable for the zinc(II) complex compound according to the invention, for example, as fire retardant, mordant, siccative, resin resin, anti-friction agent, lubricant, corrosion protection agent, zinc coating agent, galvanizing agent, impregnation agent, stabilizer, preservative, fungistatic, hydrophobing agents, adhesive promoters, starting product for pigments, cleaning agent additive, dyeing auxiliary agent, textile auxiliary agent, absorption agent, etching agent, fertilizer, fodder, for cosmetic purposes, for example, as a deodorant, for pharmaceutical purposes, for example, as a dermatic agent, a wound treatment agent, antiseptic, zinc supplement, depot active substance, etc.

EXAMPLES

Description of the Measurement Methods

The infrared spectra were measured with a Perkin-Elmer 1600 FT-IR apparatus (horizontal ATR measurement unit with ZnSe crystals; measurement window 4000-650 $cm^{-1}$). Undiluted liquid samples were applied as films, and solid samples were dissolved in $CH_2Cl_2$. The absorption bands are indicated using wave numbers ($cm^{-1}$).

The $^1$H-NMR spectra were measured on a Bruker DPX-300 spectrometer at 300.13 MHz; the chemical δ shifts are indicated in ppm relative to tetramethylsilane (TMS). No distinction was made between true and pseudo coupling patterns.

The viscosity was measured with a thermostated Physica MCR 300 cone-plate viscometer (cone diameter 20 mm, cone angle 1°, cone tip-plate distance 0.05 mm, shear rate 0.1 to 100 $s^{-1}$).

The UV-vis spectra of samples (40 mg/L) dissolved in dichloromethane were measured in 1 cm quartz cuvettes with a Varian Cary 50 spectrometer in the wavelength range 800-200 nm. The extinction maxima $\lambda_{max}$ are indicated in nm, and the associated extinction coefficients ε are given in $l \cdot g^{-1} \cdot cm^{-1}$ in parentheses.

Preparation of the Zinc(II) Complex Compounds

General Preparation Procedure A

In a round-bottom flask, dried zinc(II) bis(acetylacetonate) and 1,3-ketoamide were mixed, and the mixture was heated under stirring for 3 hours at 80° C. Subsequently, the volatile components were removed from the reaction mixture in a vacuum.

General Preparation Procedure B

In a round-bottom flask, a mixture of dried zinc(II) bis(acetylacetonate) and 1,3-ketoamide in tetraethylene glycol dimethyl ether (TEGDME) was heated under stirring for 3 hours at 80° C. Subsequently, the reaction mixture was cooled to room temperature.

Example 1

Zinc(II) bis(N,N-diethyl-3-oxobutane amidate)

3.39 g Zinc(II) bis(acetylacetonate) and 4.11 g N,N-diethyl-3-oxobutane amide were reacted according to General Preparation Procedure A. The product consisted of 4.52 g of a yellow solid.

FT-IR: 2974, 2932, 2873, 1721, 1638, 1556, 1513, 1435, 1387, 1358, 1308, 1274, 1208, 1164, 1096, 1080, 1007, 955, 921, 828, 765, 728, 668.

UV-vis: 270 (0.22). (compare zinc(II) bis(acetylacetonate): 294 (0.21) and 280 (0.27).)

Example 2

Zinc(II) bis(N,N-diethyl-3-oxobutane amidate) in TEGDME 5.27 g Zinc(II) bis(acetylacetonate) and 6.60 g N,N-diethyl-3-oxobutane amide were reacted in 10.02 g TEGDME according to General Preparation Procedure B. The product consisted of 21.89 g of a yellow solution.

Example 3

Zinc(II) bis(N,N-dibutyl-3-oxobutane amidate)

2.76 g Zinc(II) bis(acetylacetonate) and 4.69 g N,N-dibutyl-3-oxobutane amide were reacted according to General Preparation Procedure A. The product consisted of 5.66 g of a viscous, orange-colored oil.

$^1$H-NMR (CDCl$_3$): δ 0.85-1.0 (m, 12H, CH$_3$CH$_2$), 1.2-1.4 (m, 8H, CH$_2$CH$_3$), 1.4-1.6 (m, 8H, CH$_2$CH$_2$CH$_3$), 1.95 (s, 6H, MeCO), 3.1-3.1 (m, 4H, NCH$_2$), 3.25-3.35 (m, 4H, NCH$_2$), 4.8 (s, 2H, CHCO).

FT-IR: 2955, 2929, 2870, 2359, 1581, 1555, 1511, 1463, 1388, 1366, 1290, 1227, 1204, 997, 947, 764, 732.

Example 4

Zinc(II) bis(N,N-dibutyl-3-oxobutane amidate) in TEGDME 2.69 g Zinc(II) bis(acetylacetonate) and 4.70 g N,N-dibutyl-3-oxobutane amide were reacted in 8.37 g TEGDME according to General Preparation Procedure B. The product consisted of 15.76 g of a yellow solution.

Example 5

Zinc(II) bis(N,N-bis(2-ethylhexyl)-3-oxobutane amidate) in TEGDME 1.67 g Zinc(II) bis(acetylacetonate) and 4.47 g N,N-bis(2-ethylhexyl)-3-oxobutane amide were reacted in 4.40 g TEGDME according to General Preparation Procedure B. The product consisted of 10.54 g of a yellow solution.

Example 6

Zinc(II) bis(N-cyclohexyl-N-methyl-3-oxobutane amidate) in TEGDME 2.71 g Zinc(II) bis(acetylacetonate) and 4.38 g N-cyclohexyl-N-methyl-3-oxobutane amide were reacted in 8.05 g TEGDME according to General Preparation Procedure B. The product consisted of 15.14 g of a yellowish solution.

Example 7

Zinc(II) bis(N,N-bis(2-methoxyethyl)-3-oxobutane amidate))

3.00 g Zinc(II) bis(acetylacetonate) and 4.79 g N,N-bis(2-methoxyethyl)-3-oxobutane amide were reacted according to General Preparation Procedure A. The product consisted of 5.75 g of a viscous, orange-colored oil.

$^1$H-NMR (CDCl$_3$): δ 1.95 (s, 6H, MeCO), 3.3-3.35 (m, 12H, OMe), 3.45-3.6 (m, 16H, NCH$_2$ and OCH$_2$), 4.85 (s, 2H, CHCO).

FT-IR: 2981, 2925, 2891, 2830, 2359, 2340, 1718, 1636, 1574, 1515, 1383, 1360, 1262, 1193, 1112, 1014, 961, 926, 768, 732, 668.

Example 8

Zinc(II) bis(N,N-dibutyl-3-oxoheptane amidate)

2.70 g Zinc(II) bis(acetylacetonate) and 5.65 g N,N-dibutyl-3-oxoheptane amide were reacted according to General Preparation Procedure A. The product consisted of 6.25 g of a yellow oil.

$^1$H-NMR (CDCl$_3$): δ 0.8-1.0 (m, 18H, CH$_3$CH$_2$), 1.25-1.4 (m, 12H, CH$_3$CH$_2$), 1.45-1.65 (m, 12H, CH$_2$CH$_2$CH$_3$), 2.1-2.2 (t, 4H, CH$_2$CO), 3.1-3.2 (m, 4H, NCH$_2$), 3.25-3.35 (m, 4H, NCH$_2$), 4.75 (s, 2H, CHCO).

FT-IR: 2954, 2929, 2870, 1552, 1511, 1461, 1430, 1393, 1369, 1290, 1223, 1102, 951, 768, 731.

Example 9

Zinc(II) bis(N,N-bis(2-ethylhexyl)-3-oxoheptane amidate) in TEGDME 2.58 g Zinc(II) bis(acetylacetonate) and 7.91 g N,N-bis(2-ethylhexyl)-3-oxoheptane amide were reacted in 4.03 g TEGDME according to General Preparation Procedure B. The product consisted of 14.52 g of a yellow solution.

Example 10

Zinc(II) bis(N,N-bis(2-methoxyethyl)-3-oxoheptane amidate)

2.70 g Zinc(II) bis(acetylacetonate) and 5.57 g N,N-bis(2-methoxyethyl)-3-oxoheptane amide were reacted according to General Preparation Procedure A. The product consisted of 6.01 g of a viscous, orange-colored oil.

$^1$H-NMR (CDCl$_3$): δ 0.85-0.95 (t, 12H, CH$_3$CH$_2$), 1.25-1.4 (m, 8H, CH$_2$CH$_2$), 1.5-1.65 (m, 8H, CH$_2$CH$_2$CH$_3$), 2.1-2.2 (t, 4H, CH$_2$CH$_2$CO), 3.3-3.4 (m, 6H, OMe), 3.4-3.6 (m, 8H, OCH$_2$ and NCH$_2$), 4.8 (s, 2H, CHCO).

FT-IR: 2953, 2926, 2871, 1553, 1511, 1454, 1383, 1359, 1273, 1195, 1113, 1011, 950, 927, 768, 728, 668.

Example 11

Zinc(II) bis(N,N-bis(2-methoxyethyl)-3-oxo-heptane amidate) in TEGDME 2.61 g Zinc(II) bis(acetylacetonate) and 5.66 g N,N-bis(2-methoxyethyl)-3-oxoheptane amidate were reacted in 6.04 g TEGDME according to General Preparation Procedure B. The product consisted of 14.31 g of a yellowish solution.

Example 12

Zinc(II) bis(N,N-dibutyl-3-oxo-3-phenylpropane amidate)

1.99 g Zinc(II) bis(acetylacetonate) and 4.37 g N,N-dibutyl-3-oxo-3-phenylpropane amide were reacted according to General Preparation Procedure A. The product consisted of 5.01 g of a viscous, orange-colored oil.

$^1$H-NMR (CDCl$_3$): δ 0.85-1.0 (m, 12H, CH$_3$CH$_2$), 1.25-1.45 (m, 8H, CH$_2$CH$_3$), 1.45-1.7 (m, 8H, CH$_2$CH$_2$CH$_3$), 3.2-3.45 (m, 8H, NCH$_2$), 5.45 (s, 2H, CHCO), 7.35-7.5 (m, 6H, arom-H), 7.75-7.8 (m, 2H, arom-H), 7.95-8.1 (m, 2H, arom-H).

FT-IR: 2955, 2928, 2869, 2359, 2339, 1584, 1548, 1499, 1482, 1462, 1366, 1292, 1214, 1111, 1020, 914, 760, 696.

Example 13

Zinc(II) bis(N,N-bis(2-ethylhexyl)-3-oxo-3-phenylpropane amidate) in TEGDME 2.65 g Zinc(II) bis(acetylacetonate) and 8.57 g N,N-bis(2-ethylhexyl)-3-oxo-3-phenylpropane amide were reacted in 4.84 g TEGDME according to General Preparation Procedure B. The product consisted of 16.06 g of a yellowish solution.

Example 14

Zinc(II) bis(N,N-dibutyl-2-oxocyclopentane carboxamidate) in TEGDME 2.71 g Zinc(II) bis(acetylacetonate) and 5.47 g N,N-dibutyl-2-oxocyclopentane carboxamide were reacted in 7.57 g TEGDME according to General Preparation Procedure B. The product consisted of 15.75 g of a yellow solution.

Example 15

Zinc(II) bis(N,N-bis(2-ethylhexyl)-2-oxocyclopentane carboxamidate) in TEGDME 2.77 g Zinc(II) bis(acetylacetonate) and 7.96 g N,N-bis(2-ethylhexyl)-2-oxocyclopentane carboxamide were reacted in 5.02 g TEGDME according to General Preparation Procedure B. The product consisted of 15.75 g of a yellowish solution.

Two-Component Polyurethane Compositions

Examples 16 to 17 and Comparative Examples V1 to V5

For the preparation of the first component, for each example, a polyethertriol (Voranol® CP 4755, from Dow) and a catalyst according to Table 1 were intimately mixed in a centrifugal mixer (SpeedMixer™ DAC 150, FlackTek Inc.) for 30 s at 3000 rpm. A portion of the freshly prepared first component was subsequently filled into an aluminum tube which was painted on the inside, this tube was closed in an airtight manner and stored for 7 days in a convection oven at 60° C.

For each example, the remaining portion of the freshly prepared first component was mixed, in the described manner, with a modified diphenylmethane diisocyanate (Desmodur® CD-L, from Bayer) which is liquid at room temperature as second component according to Table 1 to form a polyurethane composition.

Likewise, for each example, the first component which had been stored for 7 days at 60° C. was mixed with the second component according to Table 1 in the same manner to form a polyurethane composition.

TABLE 1

Two-component polyurethane compositions (quantities in parts by weight).

| Example | 16 | 17 | V1 | V2 | V3 | V4 | V5 |
|---|---|---|---|---|---|---|---|
| First component: | | | | | | | |
| Voranol ® CP 4755 | 50 | 50 | 50 | 50 | 50 | 50 | 50 |
| Catalyst Example 2 | 0.34 | — | — | — | — | — | — |
| Catalyst Example 9 | — | 0.20 | — | — | — | — | — |
| Zn(acac)$_2$$^a$ | — | — | 2.05 | — | — | — | — |
| Zinc octoate$^b$ | — | — | — | 0.68 | — | — | — |
| DBTDL$^c$ | — | — | — | — | 0.46 | — | — |
| Coscat ® 83$^d$ | — | — | — | — | — | 0.02 | — |
| DABCO 33-LV ®$^e$ | — | — | — | — | — | — | 0.10 |
| mmol equiv./100 g$^f$ | 0.56 | 0.24 | 3.27 | 4.10 | 0.13 | 0.03 | 1.07 |
| Second component: | | | | | | | |
| Desmodur ® CD-L | 5.10 | 5.10 | 5.10 | 5.10 | 5.10 | 5.10 | 5.10 |

$^a$24% suspension of zinc(II) bis(acetylacetonate) in dimethyl sulfoxide.
$^b$Zinc-2-ethylhexanoate (22% Zn, from Alfa Aesar).
$^c$10% solution of dibutyltin dilaurate in diisodecyl phthalate.
$^d$Bismuth-tris(neodecanoate) in neodecanoic acid (16% Bi, from Erbslöh).
$^e$33% solution of 1,4-diazabicyclo[2.2.2]octane in dipropylene glycol (from Air Products).
$^f$mmol equivalents of metal atoms or amino groups of the catalyst per 100 g of the composition.

The polyurethane compositions were checked to determine the appearance, tack-free time, bubble formation and Shore A hardness, in particular in each case both for the composition with the freshly prepared first component and also for the composition with the first component which had been stored for 7 days at 60° C. Moreover, exclusively for the composition with the freshly prepared first component, the mechanical properties were also measured in the tensile test, in particular before and after various storage procedures for accelerated aging of the samples.

The appearance of the composition was evaluated purely visually and ranked as "clear," "turbid" or "inhomogeneous" ("inh.").

For the determination of the tack-free time (skin formation time), the room-temperature compositions were applied in a layer thickness of approximately 3 mm to cardboard, and, under standard atmospheric conditions ("NK" 23±1° C., 50±5% relative humidity), the time was determined in each case until the first time that no residues remained on the pipette after slightly tapping the surface of composition with a pipette made of LDPE.

The bubble formation was evaluated visually using the number ("many," "some," "none") of gas bubbles which occurred in the composition prepared for the determination of the skin formation time during its curing.

The Shore A hardness was determined according to DIN 53505 on test specimens that had been cured for 7 days under standard atmospheric conditions.

For the determination of the mechanical properties in the tensile test, films having a thickness of approximately 3 mm were prepared from the compositions, by pouring the composition into a flat PTFE mold and curing it for 7 days under standard atmospheric conditions. Tack-free, elastic films were obtained. From the films, dumbbell shaped samples were punched, having a length of 75 mm, with a bar length of 30 mm, and a bar width of 4 mm, and some of them were tested according to DIN EN 53504 at a traction rate of 200 mm/min to determine the tensile strength, the elongation at rupture, and the E modulus (at an elongation of 0.5 to 5.0%). The rest of the dumbbells were stored for 1 day at 100° C. in the convection oven, for example, for 10 days under "cataplasm" (40° C. and 100% relative humidity) or for 10 days under "cataplasm" as well as for 1 day at 100° C., whereafter, in each case, they were kept for one day under standard atmospheric conditions and tested as described according to DIN EN 53504.

The results of these tests are listed in Table 2.

As can be seen in Table 2, the two-component polyurethane compositions with the catalysts according to the invention represent clear, homogeneous mixtures that have relatively short skin formation times both before and after storage and cure without bubbles to form a material with a relatively high strength and satisfactory resistance.

Examples 18 to 19 and Comparative Examples V6 to V10

For the preparation of the first component, for each example, a polyether triol (Voranol® CP 4755, from Dow), a polyether diol (Acclaim® 4200, from Bayer), and a catalyst according to Table 3 were intimately mixed in a centrifugal mixer (SpeedMixer™ DAC 150, FlackTek Inc.) for 30 s at 3000 rpm. A portion of the freshly prepared first component was then filled into an internally painted aluminum tube; this tube was closed in an airtight manner, and stored for 7 days in a convection oven at 60° C.

For each example, the rest of the freshly prepared first component was mixed in the described manner with a modified diphenylmethane diisocyanate (Desmodur® CD-L, from Bayer), which is liquid at room temperature, as second component according to Table 3 to form a polyurethane composition.

Likewise, for each example, the first component which had been stored for 7 days at 60° C. was mixed with the second component according to Table 3 in the same manner to form a polyurethane composition.

TABLE 2

Properties of the two-component polyurethane compositions

| Example | 16 | 17 | V1 | V2 | V3 | V4 | V5 |
|---|---|---|---|---|---|---|---|
| Composition with freshly prepared first component: | | | | | | | |
| Appearance | clear | clear | inh. | clear | clear | clear | clear |
| Skin formation time (min) | 7 | 22 | 6 | 20 | 10 | 3 | 15 |
| Shore A hardness | 31 | 38 | 16 | 29 | 48 | 44 | 33 |
| Bubble formation | none | none | none | none | some | none | some |
| Tensile strength (MPa): 7 d/NK | 0.76 | 0.72 | 0.61 | 0.85 | 0.76 | 0.54 | 0.90 |
| + 10 d/cataplasm | 0.66 | 0.79 | 0.67 | 0.77 | 0.71 | 0.79 | 0.82 |
| + 1 d/100° C. | 0.87 | 0.89 | 0.74 | 0.88 | 0.60 | 0.73 | 0.86 |
| + 10 d/cataplasm + 1 d/100° C. | 0.92 | 0.77 | 0.69 | 0.90 | 0.65 | 0.73 | 0.89 |
| Elongation at rupture (%): 7 d/NK | 84 | 81 | 125 | 87 | 65 | 42 | 100 |
| + 10 d/cataplasm | 64 | 93 | 142 | 71 | 56 | 73 | 85 |
| + 1 d/100° C. | 93 | 96 | 127 | 99 | 168 | 72 | 105 |
| + 10 d/cataplasm + 1 d/100° C. | 108 | 78 | 129 | 107 | 170 | 74 | 108 |
| E modulus (MPa): 7 d/NK | 1.29 | 1.22 | 0.70 | 1.54 | 1.68 | 1.46 | 1.44 |
| + 10 d/cataplasm | 1.38 | 1.21 | 0.80 | 1.53 | 1.68 | 1.56 | 1.47 |
| + 1 d/100° C. | 1.36 | 1.45 | 1.08 | 1.37 | 0.60 | 1.49 | 1.23 |
| + 10 d/cataplasm + 1 d/100° C. | 1.24 | 1.41 | 0.93 | 1.40 | 0.71 | 1.41 | 1.23 |
| Composition with stored first component: | | | | | | | |
| Appearance | clear | clear | n.d. | clear | clear | clear | clear |
| Skin formation time (min) | 8 | 22 | n.d. | 21 | 10 | 45 | 15 |
| Shore A hardness | 22 | 44 | n.d. | 34 | 48 | 45 | 32 |
| Bubble formation | none | none | n.d. | none | some | some | some | n.d. = not determined.

TABLE 3

Two-component polyurethane compositions
(quantities in parts by weight)

| Example | 18 | 19 | V6 | V7 | V8 | V9 | V10 |
|---|---|---|---|---|---|---|---|
| First component: | | | | | | | |
| Voranol ® CP 4755 | 33.3 | 33.3 | 33.3 | 33.3 | 33.3 | 33.3 | 33.3 |
| Acclaim ® 4200 | 16.7 | 16.7 | 16.7 | 16.7 | 16.7 | 16.7 | 16.7 |
| Catalyst Example 2 | 0.18 | — | — | — | — | — | — |
| Catalyst Example 9 | — | 0.25 | — | — | — | — | — |
| Zn(acac)$_2$[a] | — | — | 0.17 | — | — | — | — |
| Zinc octoate[b] | — | — | — | 0.53 | — | — | — |
| DBTDL[c] | — | — | — | — | 0.49 | — | — |
| Coscat ® 83[d] | — | — | — | — | — | 0.02 | — |
| DABCO 33-LV ®[e] | — | — | — | — | — | — | 0.14 |
| mmol equiv./100 g[f] | 0.29 | 0.29 | 0.29 | 3.20 | 0.14 | 0.03 | 1.50 |
| Second component: | | | | | | | |
| Desmodur ® CD-L | 5.00 | 5.00 | 5.00 | 5.00 | 5.00 | 5.00 | 5.00 |

[a]25% suspension of zinc(II) bis(acetylacetonate) in methyl ethyl ketone.
[b]Zinc-2-ethylhexanoate (22% Zn, from Alfa Aesar).
[c]10% solution of dibutyltin dilaurate in diisodecyl phthalate.
[d]Bismuth-tris(neodecanoate) in neodecanoic acid (16% Bi, from Erbslöh).
[e]33% solution of 1,4-diazabicyclo[2.2.2]octane in dipropylene glycol (from Air Products).
[f]mmol equivalent of metal atoms or amino groups of the catalyst per 100 g of the composition.

The polyurethane compositions were checked as described for Example 16 to determine the appearance, tack-free time, bubble formation as well as the mechanical properties in the tensile test, in particular in each case only for the composition with the freshly prepared first component.

The results of these tests are listed in Table 4.

TABLE 4

Properties of the two-component polyurethane compositions

| Example | 18 | 19 | V6 | V7 | V8 | V9 | V10 |
|---|---|---|---|---|---|---|---|
| Composition with freshly prepared first component: | | | | | | | |
| Appearance | clear | clear | inh. | clear | clear | clear | clear |
| Skin formation time (min) | 20 | 80 | 140 | 52 | 27 | 90 | 35 |
| Bubble formation | none | none | none | some | many | none | many |
| Tensile strength (MPa): 7 d/NK | 0.73 | 0.71 | 0.71 | 0.63 | 0.77 | 0.71 | 0.65 |
| + 10 d/cataplasm | 0.65 | 0.71 | 0.66 | 0.61 | 0.77 | 0.73 | 0.66 |
| + 1 d/100° C. | 0.73 | 0.76 | 0.79 | 0.57 | 0.48 | 0.70 | 0.72 |
| + 10 d/cataplasm + 1 d/100° C. | 0.83 | 0.82 | 0.80 | 0.66 | 0.52 | 0.74 | 0.69 |
| Expansion at rupture (%): 7 d/NK | 131 | 131 | 144 | 127 | 105 | 124 | 135 |
| + 10 d/cataplasm | 108 | 114 | 145 | 121 | 105 | 119 | 148 |
| + 1 d/100° C. | 147 | 138 | 157 | 122 | 341 | 137 | 193 |
| + 10 d/cataplasm + 1 d/100° C. | 120 | 137 | 137 | 158 | 303 | 178 | 181 |
| E modulus (MPa): 7 d/NK | 0.90 | 0.79 | 0.76 | 0.83 | 1.20 | 0.82 | 0.88 |
| + 10 d/cataplasm | 0.91 | 1.02 | 0.72 | 0.78 | 1.30 | 0.98 | 0.81 |
| + 1 d/100° C. | 0.98 | 0.89 | 0.94 | 0.77 | 0.20 | 0.91 | 0.69 |
| + 10 d/cataplasm + 1 d/100° C. | 1.01 | 1.08 | 1.02 | 0.83 | 0.28 | 0.80 | 0.65 |

As can be seen in Table 4, the two-component polyurethane compositions with the catalysts according to the invention represent clear, homogeneous mixtures that have relatively short skin formation times and that cure without bubbles to form a material with a relatively high strength and satisfactory resistance.

Examples 20 to 31

As described for Example 16, for the preparation of the first component, in each case, a polyether triol (Voranol® CP 4755, from Dow) and a catalyst according to Table 5 were mixed. A portion of the freshly prepared first component was then filled into an internally painted aluminum tube; this tube was closed in an airtight manner and stored for 7 days in a convection oven at 60° C.

The rest of the freshly prepared first component was mixed for each example in the manner described for Example 16 with a modified diphenylmethane diisocyanate (Desmodur® CD-L, from Bayer), which is liquid at room temperature, as second component according to Table 5 to form a polyurethane mixture.

Likewise, for each example, the first component which had been stored for 7 days at 60° C. was mixed with the second component according to Table 5 in the same manner to form a polyurethane composition.

The polyurethane compositions were checked as for Example 16 to determine the appearance, tack-free time, bubble formation and Shore A hardness as well as the mechanical properties in the tensile test.

The results of these tests are listed in Table 6.

TABLE 5

Two-component polyurethane compositions

| Example | 20 | 21 | 22 | 23 | 24 | 25 | 26 | 27 | 28 | 29 | 30 | 31 |
|---|---|---|---|---|---|---|---|---|---|---|---|---|
| First component: | | | | | | | | | | | | |
| Voranol ® CP 4755 | 30 | 30 | 30 | 30 | 30 | 30 | 30 | 30 | 30 | 30 | 30 | 30 |
| Catalyst Example 2 | 0.76 | 0.38 | — | — | — | — | — | — | — | — | — | — |
| Catalyst Example 4 | — | — | 1.09 | 0.54 | — | — | — | — | — | — | — | — |
| Catalyst Example 5 | — | — | — | — | 1.22 | — | — | — | — | — | — | — |
| Catalyst Example 6 | — | — | — | — | — | 1.03 | — | — | — | — | — | — |
| Catalyst Example 8 | — | — | — | — | — | — | 0.42 | — | — | — | — | — |
| Catalyst Example 9 | — | — | — | — | — | — | — | 1.03 | — | — | — | — |
| Catalyst Example 11 | — | — | — | — | — | — | — | — | 1.04 | — | — | — |
| Catalyst Example 13 | — | — | — | — | — | — | — | — | — | 1.12 | — | — |
| Catalyst Example 14 | — | — | — | — | — | — | — | — | — | — | 1.11 | — |
| Catalyst Example 15 | — | — | — | — | — | — | — | — | — | — | — | 0.99 |
| mmol equiv./100 g$^a$ | 2.05 | 1.03 | 2.06 | 1.04 | 2.14 | 2.05 | 2.05 | 2.04 | 2.11 | 2.05 | 2.12 | 1.94 |
| Second component: | | | | | | | | | | | | |
| Desmodur ® CD-L | 3.10 | 3.10 | 3.10 | 3.10 | 3.10 | 3.10 | 3.10 | 3.10 | 3.10 | 3.10 | 3.10 | 3.10 |

$^a$mmol equivalent of zinc atoms of the catalyst per 100 g of the composition.

TABLE 6

Properties of the two-component polyurethane compositions.

| Example | 20 | 21 | 22 | 23 | 24 | 25 | 26 | 27 | 28 | 29 | 30 | 31 |
|---|---|---|---|---|---|---|---|---|---|---|---|---|
| Composition with freshly prepared first component: | | | | | | | | | | | | |
| Appearance | clear | clear | clear | clear | clear | clear | clear | clear | clear | clear | clear | clear |
| Skin formation time (min) | 7 | 25 | 3 | 6 | 3 | 3 | 1 | 3 | 3 | 4 | 2 | 2 |
| Shore A hardness | 31 | 32 | 39 | 42 | 33 | 37 | 38 | 38 | 41 | 43 | 38 | 42 |
| Bubble formation | none | none | none | none | none | none | none | none | none | none | none | none |
| Composition with stored first component: | | | | | | | | | | | | |
| Appearance | clear | clear | clear | clear | clear | clear | clear | clear | clear | clear | clear | clear |
| Skin formation time (min) | 8 | 24 | 2 | 5 | 3 | 2 | 2 | 3 | 3 | 2 | 2 | 1 |
| Shore A hardness | 22 | 28 | 40 | 43 | 34 | 39 | 45 | 38 | 43 | 43 | 43 | 41 |
| Bubble formation | some | none | some | none | none | none | none | none | none | none | none | some |

As can be seen in Table 6, the two-component polyurethane compositions with the catalysts according to the invention represent clear, homogeneous mixtures which have relatively short skin formation times both before and after storage and which cure largely without bubbles to form a material with a satisfactory Shore A hardness.

The invention claimed is:

1. A method for preparing a zinc(II) complex compound of formula $Zn(L)_x(Y)_{2-x}$, where x stands for 1 or 2, Y for a ligand with a single negative charge, and L for a ligand, wherein a 1,3-ketoamide of formula

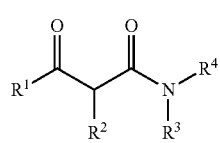

wherein $R^1$ and $R^2$, independently of one another, stand for a hydrogen residue, a monovalent saturated or unsaturated hydrocarbon residue having 1 to 10 carbon atoms, or together stand for a bivalent alkylene residue having 3 to 6 carbon atoms, and $R^3$ and $R^4$, independently of one another, stand for a hydrogen residue, a monovalent saturated hydrocarbon residue, which optionally contains heteroatoms, having 1 to 12 carbon atoms, or together stand for a bivalent alkylene residue, which also contains heteroatoms, having 3 to 6 carbon atoms, wherein the Zn(II) complex compound is not a zinc(II) chelate of 2,2,6,6-tetramethyl-4-[N-n-butylamine-N-(1',3'-dioxobutyl)]-piperidine enolate, is reacted with a zinc(II) salt or a zinc(II) complex.

2. The method according to claim 1, wherein the ratio between the zinc(II) salt or the zinc(II) complex and the 1,3-ketoamide is in the range from 1:2 to 1:6.

3. The method according to claim 1, wherein zinc(II) bis(acetylacetonate) is used as zinc(II) complex.

4. A two-component polyurethane composition, comprising:
at least one polyol as first component,
at least one polyisocyanate as second component, and
at least one zinc(II) complex compound of formula $Zn(L)_x(Y)_{2-x}$, where x stands for 1 or 2, Y for a ligand with a single negative charge, and L for a ligand of formula (I),

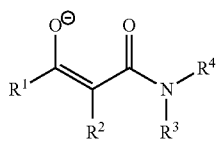

wherein R¹ and R², independently of one another, stand for a hydrogen residue, a monovalent saturated or unsaturated hydrocarbon residue having 1 to 10 carbon atoms, or together stand for a bivalent alkylene residue having 3 to 6 carbon atoms, and R³ and R⁴, independently of one another, stand for a hydrogen residue, a monovalent saturated hydrocarbon residue, which optionally contains heteroatoms, having 1 to 12 carbon atoms, or together stand for a bivalent alkylene residue, which also contains heteroatoms, having 3 to 6 carbon atoms, wherein the Zn(II) complex compound is not a zinc(II) chelate of 2,2,6,6-tetramethyl-4-[N-n-butylamine-N-(1',3'-dioxobutyl)]-piperidine enolate.

5. The two-component polyurethane composition according to claim 4, wherein the polyol is a polyether polyol and the polyisocyanate is a diisocyanate.

6. The two-component polyurethane composition according claim 4, wherein the zinc(II) complex compound represents 0.015 to 15 mmol equivalents of zinc atoms per 100 g of the composition.

7. The two-component polyurethane composition according to claim 4, wherein the zinc(II) complex compound is contained in the first component.

8. The two-component polyurethane composition according to claim 4 as casting composition, sealant, adhesive, coating, covering, paint, primer, molded part, elastomer for construction and industry.

9. The method according to claim 1, where R¹ stands for an alkyl residue having 1 to 4 carbons, for a phenyl residue, or together with R² stands for a bivalent alkylene residue having 3 to 4 carbon atoms.

10. The method according to claim 1, where R² stands for a hydrogen residue.

11. The method according to claim 1, where R³ stands for a hydrogen residue, an alkyl residue having 1 to 8 carbon atoms, a cycloalkyl residue having 5 to 6 carbons, a hydroxyalkyl residue having 1 to 4 carbon atoms, an alkyl ether residue having 1 to 4 carbon atoms, or together with R⁴ stands for a bivalent alkylene residue of formula

—(CH₂)ₙ—X—(CH₂)ₙ— with X=O, NR, wherein R is a monovalent alkyl residue having 1 to 4 carbon atoms, or S, and n=2 to 6.

12. The method according to claim 1, where R⁴ stands for a hydrogen residue, an alkyl residue having 1 to 8 carbon atoms, a cycloalkyl residue having 5 to 6 carbon atoms, a hydroxyalkyl residue having 1 to 4 carbon atoms or an alkyl ether residue having 1 to 4 carbon atoms.

13. The method according to claim 1, where x stands for 2.

14. The two-component polyurethane composition according to claim 4, where R¹ stands for an alkyl residue having 1 to 4 carbons, for a phenyl residue, or together with R² stands for a bivalent alkylene residue having 3 to 4 carbon atoms.

15. The two-component polyurethane composition according to claim 4, where R² stands for a hydrogen residue.

16. The two-component polyurethane composition according to claim 4, where R³ stands for a hydrogen residue, an alkyl residue having 1 to 8 carbon atoms, a cycloalkyl residue having 5 to 6 carbons, a hydroxyalkyl residue having 1 to 4 carbon atoms, an alkyl ether residue having 1 to 4 carbon atoms, or together with R⁴ stands for a bivalent alkylene residue of formula

—(CH₂)ₙ—X—(CH₂)ₙ— with X=O, NR, wherein R is a monovalent alkyl residue having 1 to 4 carbon atoms, or S, and n=2 to 6.

17. The two-component polyurethane composition according to claim 4, where R⁴ stands for a hydrogen residue, an alkyl residue having 1 to 8 carbon atoms, a cycloalkyl residue having 5 to 6 carbon atoms, a hydroxyalkyl residue having 1 to 4 carbon atoms or an alkyl ether residue having 1 to 4 carbon atoms.

18. The two-component polyurethane composition according to claim 4, where x stands for 2.

19. A one-component polyurethane composition, comprising:
at least one isocyanate group containing polyurethane prepolymer, and
at least one zinc(II) complex compound of formula Zn(L)ₓ(Y)₂₋ₓ, where x stands for 1 or 2, Y for a ligand with a single negative charge, and L for a ligand of formula (I),

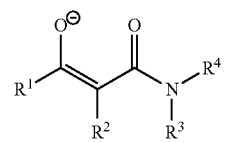

wherein R¹ and R², independently of one another, stand for a hydrogen residue, a monovalent saturated or unsaturated hydrocarbon residue having 1 to 10 carbon atoms, or together stand for a bivalent alkylene residue having 3 to 6 carbon atoms, and R³ and R⁴, independently of one another, stand for a hydrogen residue, a monovalent saturated hydrocarbon residue, which optionally contains heteroatoms, having 1 to 12 carbon atoms, or together stand for a bivalent alkylene residue, which also contains heteroatoms, having 3 to 6 carbon atoms, wherein the Zn(II) complex compound is not a zinc(II) chelate of 2,2,6,6-tetramethyl-4-[N-n-butylamine-N-(1',3'-dioxobutyl)]-piperidine enolate.

* * * * *